(12) United States Patent
Perler et al.

(10) Patent No.: US 10,092,281 B2
(45) Date of Patent: Oct. 9, 2018

(54) SURGICAL RETRACTOR

(71) Applicants: Adam D. Perler, St. Petersburg, FL (US); James A. Zoellner, Avon, IN (US)

(72) Inventors: Adam D. Perler, St. Petersburg, FL (US); James A. Zoellner, Avon, IN (US)

(73) Assignee: InMotus Medical LLC, Carmel, IN (US)

( * ) Notice: Subject to any disclaimer, the term of this patent is extended or adjusted under 35 U.S.C. 154(b) by 104 days.

(21) Appl. No.: 14/876,747

(22) Filed: Oct. 6, 2015

(65) Prior Publication Data

US 2017/0095241 A1    Apr. 6, 2017

(51) Int. Cl.
     *A61B 17/02*      (2006.01)
     *A61B 90/30*      (2016.01)
     *A61B 17/00*      (2006.01)

(52) U.S. Cl.
     CPC .......... *A61B 17/0206* (2013.01); *A61B 17/02* (2013.01); *A61B 90/30* (2016.02); *A61B 2017/00407* (2013.01); *A61B 2017/00424* (2013.01); *A61B 2017/00734* (2013.01); *A61B 2090/309* (2016.02)

(58) Field of Classification Search
     CPC ............................ A61B 90/30; A61B 17/0206
     See application file for complete search history.

(56) References Cited

U.S. PATENT DOCUMENTS

| | | | |
|---|---|---|---|
| 3,750,652 | A | 8/1973 | Sherwin |
| 4,817,587 | A | 4/1989 | Janese |
| 5,052,373 | A | 10/1991 | Michelson |
| 5,979,452 | A | 11/1999 | Fogarty et al. |
| 6,050,266 | A | 4/2000 | Federico et al. |
| 6,322,500 | B1 | 11/2001 | Sikora et al. |
| 6,348,036 | B1 | 2/2002 | Looney et al. |
| 6,364,832 | B1 | 4/2002 | Propp |
| 6,416,468 | B2 | 7/2002 | Deckman et al. |
| 6,652,454 | B2 | 11/2003 | Hu et al. |

(Continued)

FOREIGN PATENT DOCUMENTS

WO        8904145 A1    5/1989

*Primary Examiner* — Ellen C Hammond
(74) *Attorney, Agent, or Firm* — David Meibos; Maywood IP Law (57) ABSTRACT

A surgical retractor and method for retracting tissue in a patient is anatomically designed for particular muscles and includes a light source the light beam of which is positionable relative to the surgical retractor. The surgical retractor has a pair of retraction blades carried on separate retraction portions held open by ratchet assemblies. Blades are manually retracted and held open by automatically engaging ratchet fingers and are designed to match muscle curvature, minimizing various risks and incision size. The first retraction portion carries the first blade and includes tines each with ratchet grooves, while the second retraction portion carries the second blade on a carriage that is movably carried on the tines. Resilient spring actuated fingers associated with the carriage has ratchet grooves that co-act with the ratchet grooves of the tines to provide the ratchet assemblies between the retraction portions that regulates movement of the carriage and the second blade relative to the first blade.

20 Claims, 11 Drawing Sheets

(56) References Cited

U.S. PATENT DOCUMENTS

| | | | |
|---|---|---|---|
| 7,326,177 B2 | 2/2008 | Williamson, IV et al. | |
| 7,481,766 B2 | 1/2009 | Lee et al. | |
| 7,981,029 B2 | 7/2011 | Branch et al. | |
| 8,317,693 B2 | 11/2012 | Grey et al. | |
| 8,845,527 B2 | 9/2014 | Crenshaw et al. | |
| 8,979,749 B2 | 3/2015 | Gorek et al. | |
| 2007/0060795 A1* | 3/2007 | Vayser | A61B 1/32 600/245 |
| 2007/0066872 A1 | 3/2007 | Morrison et al. | |
| 2009/0076334 A1 | 3/2009 | Chen | |
| 2009/0156902 A1 | 6/2009 | Jonathan et al. | |
| 2010/0317928 A1 | 12/2010 | Subramaniam | |
| 2011/0098537 A1 | 4/2011 | Justis et al. | |
| 2011/0190588 A1 | 8/2011 | McKay | |
| 2011/0313256 A1* | 12/2011 | Raymond | A61B 17/02 600/231 |
| 2012/0059226 A1 | 3/2012 | Funt | |
| 2012/0143011 A1 | 6/2012 | Gorek | |
| 2013/0190575 A1 | 7/2013 | Mast et al. | |
| 2013/0197313 A1 | 8/2013 | Wan | |
| 2015/0018627 A1 | 1/2015 | Vayser et al. | |
| 2016/0151058 A1* | 6/2016 | Ferro | A61B 17/02 600/215 |

\* cited by examiner

SURGICAL RETRACTOR

FIELD OF THE INVENTION

The present disclosure relates to surgical retractors and devices for stabilizing tissue during a surgical procedure and, particularly, to surgical retractors for use in lower extremity, upper extremity, abdominal, rectal and other areas of the body during a surgical procedure.

BACKGROUND

Many surgical procedures necessitate the use of one or more surgical devices to retract tissue at the surgical site. Such surgical devices are generally known as surgical retractors. A wide variety of surgical retractors have been patented, some for general use and some for specific use. Many of these surgical retractors however, fail to provide any advantages such as, but not limited to, a less complicated and safer surgical procedure that can reduce the risk of nerve damage, anatomical deformity, and cross-contamination, reduce tension on the retracted site, and provide limited incision length.

Also, many surgical retractors do not take into account the anatomy of the surgical site and thus are not ergonomically designed. If the surgical retractor is not designed and/or made for a specific procedure and/or tissue (e.g. tissue, muscle, muscles, or muscle groups), the risk of damage as noted above is greater. In cases wherein no specific surgical retractor is available, surgical retractors or other surgical instruments not designed for the specific procedure may be used on tissue for which it is not specifically intended. For instance, when performing a muscular lengthening of the gastrocnemius and/or soleus muscles, a vaginal, anal or rectal speculum or standard metal retractor, which is not anatomically designed for the procedure, may be used.

Moreover, it is vitally important to have adequate lighting for the surgical procedure. However, the availability or amount of light at the surgical site is typically lacking. In view of this, surgical instruments including retractors have been devised that include one or more light sources. Because heat is typically not desired during surgery, the surgical instruments and/or retractors use LEDs as the light source. However, the light sources are fixed with respect to the surgical instrument/retractor. This restricts the ability to provide light to a targeted area during surgery, such as at or in the incision or incision area. Therefore, it is easy to see that current surgical instruments/retractors restrict the visibility due to inadequate lighting within the working space.

The present invention sufficiently addresses the above concerns.

SUMMARY OF THE INVENTION

The present invention is an anatomically correct/designed (i.e. fit-for-purpose) surgical retractor with a positionable light source and method for retracting tissue in a body, such as, but not limited to, the lower extremity, upper extremity, abdominal, rectal and other areas of the body during a surgical procedure.

The surgical retractor is anatomically designed for particular tissues e.g. a muscle or muscles) of the body and includes a light source the light beam of which can be positioned to shine on a particular area of or about the surgical retractor and/or tissue in order to provide surgical exposure and illumination. The surgical retractor has a pair of retraction blades carried on separate retraction portions that are held open by ratchet assemblies. The blades in an open position create a cutting channel that is wide enough to allow use of standard scalpel blades.

Each blade may be fashioned as a loop having arms that extend from the retraction portion and which provide an open interior. The loops may be curved from their origin to their tip or otherwise provide a cured surface. This curvature may mimic the curvature of a specific muscle, muscles and/or tissue(s) intended to be retracted especially, but not necessarily, during or for a particular surgical procedure.

The light source can be an assembly that may be integral to the retractor or as/part of an assembly that is supported on the surgical retractor. An LED or other suitable light source is used along with one or more batteries. In one form, the LED can be rotated to shine or position the light beam toward and/or on the one blade or the other blade. In another form, the LED slides along a section of the surgical retractor to position the light beam accordingly. Other manners of positioning the light beam of the light source may be used and are contemplated.

In one form, the surgical retractor is characterized by a first retraction portion or arm having a first blade, and a second retraction portion or arm having a second blade, the second retraction portion movably carried on the first retraction portion. Particularly, the first retraction portion includes guide bars each with ratchet grooves of a ratchet assembly, while the second retraction portion includes a carriage movably carried on the guide bars, the second blade extending from the carriage. Resilient spring actuated fingers are associated with the carriage. The resilient spring actuated fingers have ratchet grooves that cooperate and/or co-act with the ratchet grooves of the guide bars to provide ratchet assemblies, ratchets, or ratcheting mechanisms between the first and second retraction portions that allows and prevents movement of the carriage and thus the second blade relative to the first blade.

In one embodiment, the surgical retractor is designed to be used for the gastrocnemius muscle and the soleus muscle in an intra-muscular approach such as a Baumann procedure (isolated recession of the gastrocnemius muscle and/or the soleus muscle or plantaris tendon or other procedure. It may also be used in a more traditional Strayer procedure below the myotendenous junction from a medial approach. In this approach, the blades of the retraction portions are inserted between the gastrocnemius muscle and the soleus muscle. The LED light source and battery system provides a light source whose light beam is positionable relative to the retractor to provide light on or towards one blade (e.g. adjacent the gastrocnemius muscle), the other blade (e.g. adjacent the soleus muscle), tissue, or other area.

The present surgical retractor is ergonomically designed to make it easy to maneuver and use.

The surgical retractor is preferably, but not necessarily, for single use only. However, the surgical retractor may be made for multiple use. The surgical retractor may be, and preferably is, pre-sterilized and packed in a sterile packaging reducing set-up time, cleaning costs, and risk of infections. It may be used in both adult and pediatric patients.

Although the present surgical retractor is particularly designed for use in the lower extremities, the present surgical retractor may also be used in any areas of the body such as the upper extremity, abdominal and rectal where curved blades and a lighted design may be beneficial.

BRIEF DESCRIPTION OF THE DRAWINGS

The above mentioned and other features of this invention, and the manner of attaining them, will become apparent and the invention itself will be better understood by reference to the following description of the invention taken in conjunction with the accompanying drawings, wherein.

Although the drawings represent a form of various features and components according to the present invention, the drawings are not necessarily to scale and certain features may be enhanced in order to better illustrate and explain the present invention. The exemplification set out herein is not to be construed as limiting the scope of the invention in any manner.

DETAILED DESCRIPTION

Those of skill in the art will understand that various details of the invention may be changed without departing from the spirit and scope of the invention. Furthermore, the foregoing description is for illustration only, and not for the purpose of limitation.

Referring to the Figures, there is shown a surgical retractor 10 for retracting tissue such as muscles during a surgical procedure. The surgical retractor 10 is preferably, but not necessarily, designed for one time use and thus in this form is disposable. In a multiple use form, the surgical retractor 10 may be made from a suitable metal, metal alloy, or other material that allows the surgical retractor 10 to be used multiple times and/or be cleaned and/or sterilized as necessary. The surgical retractor 10, with the exception of various components associated with light assembly 16 of the surgical retractor 10, is thus also preferably, but not necessarily, made from one or more appropriate plastics such as are known in the art. However, other suitable materials such as metal may be used. As pointed out above in the Summary of the Invention, the surgical retractor 10 may be used in lower extremity, upper extremity, abdominal, rectal and other areas of the body during a surgical procedure, particularly, but not necessarily, for retraction of muscles during a surgical procedure.

With respect to the Figures, the surgical retractor 10 is shown in several of the figures with respect to the gastrocnemius muscle G and the soleus muscle S of the body, it being appreciated that such is only illustrative, and not restrictive, of use of the present surgical retractor 10 for any particular tissue, muscle, muscles, muscle groups. One surgical procedure using the present surgical retractor 10 regarding the gastrocnemius muscle G and the soleus muscle S is a Baumann procedure where the surgical retractor is inserted between the gastrocnemius muscle G and the soleus muscle S. In particular, a Baumann procedure consists of intramuscular lengthening (recession) of the gastrocnemius muscle in the deep interval between the soleus and gastrocnemius muscles. The goal of the procedure is to increase ankle dorsiflexion when ankle movement is restricted by a contracted gastrocnemius muscle. Unlike a Vulpius procedure, which only lengthens the superficial gastrocnemius aponeurosis, the Baumann procedure can do an isolated lengthening of the deep gastrocnemius aponeurosis, but which may also lengthen the superficial soleus aponeurosis. Another procedure is the Strayer procedure which is a posteromedial surgical treatment option for clinically relevant gastrocnemius equinus contracture. Identifying and protecting the sural nerve is an important component of the procedure.

The present surgical retractor 10 may further be used to lengthen the plantaris tendon to treat ankle equinus or muscular contracture, or as a supplementary treatment of plantar fasciitis, hallux valgus, symptomatic adult acquired flatfoot, metatarsalgia, and/or diabetic foot ulcers, it being appreciated that the aforementioned surgical procedures are only illustrative, and not restrictive, of use of the present surgical retractor 10 for any particular surgical procedure or tissue.

In general, the surgical retractor 10 has a first retraction arm 12, a second retraction arm 14 (the nomenclature first and second being arbitrary), and the light assembly 16, the light assembly 16 carried on the first retraction arm 12, while the second retraction arm 14 is supported on and movable with respect to the first retraction arm 12. It should be appreciated that other configurations are contemplated.

The first retraction arm 12 is characterized by an elongated U-shaped body 18 defining an arced or curved end segment 19, a first tine 20 extending from a first end of the arced end segment 19, and a second tine 21 extending from a second end of the arced end segment 19. A tab or flange 26 extends from a side of the arced end segment 19 in order to provide a place for a user to hold and/or push against the frame 12, particularly, but not necessarily, during positioning of the surgical retractor 10. As such, an inner surface 27 of the tab 26 is preferably, but not necessarily, ribbed or otherwise textured. Of course, other manners of providing a finger or hand grip may be used and are contemplated.

The first retraction arm 12 has a first blade 30 that extends outwardly from a side of the first and second tines 20, 21. The first blade 30 is defined by a body 34 that generally forms a loop that extends from a side of the first tine 20 to a same side of the second tine 21, and defining an elongated "U" shape with an open interior. Particularly, the body 34 has an upper leg 31 that extends from the side of the first tine 20 to an arched end 33, and a lower leg 32 that extends from the side of the second tine 21 to the arched end 33. The body 34 defines a blade that is generally transverse to the first and second tines 20, 21 but which preferably, but not necessarily, includes a curvature or bow (see additionally FIGS. 10-11) in order to be anatomically correct with respect to the muscle (tissue) that the blade 30 will contact. As such, and in keeping with the present surgical retractor 10 embodied as a gastrocnemius muscle G/soleus muscle S retractor, the blade 30 is curved in like manner as the gastrocnemius muscle G. The blade 30 is made with other curvature(s) or no curvature depending on the muscle(s) or muscle group(s) being retracted. In this manner, the present surgical retractor 10 may be anatomically designed such that the surgical retractor 10 is fit for a particular purpose and/or surgical procedure.

A depression or notch 28 is provided in the upper surface of the first tine 20 proximate the arced end segment 19. The depression 28 preferably, but not necessarily, includes serrations or the like to provide a gripping area. Likewise, a depression or notch 29 is provided in the lower surface of the second tine 21 proximate the arced end segment 19. The depression 29 preferably, but not necessarily, includes serrations or the like to provide a gripping area. The serrated depressions 28 and 29 allow a user to easily grasp or hold the first retraction arm 12 during use.

Figure 9:
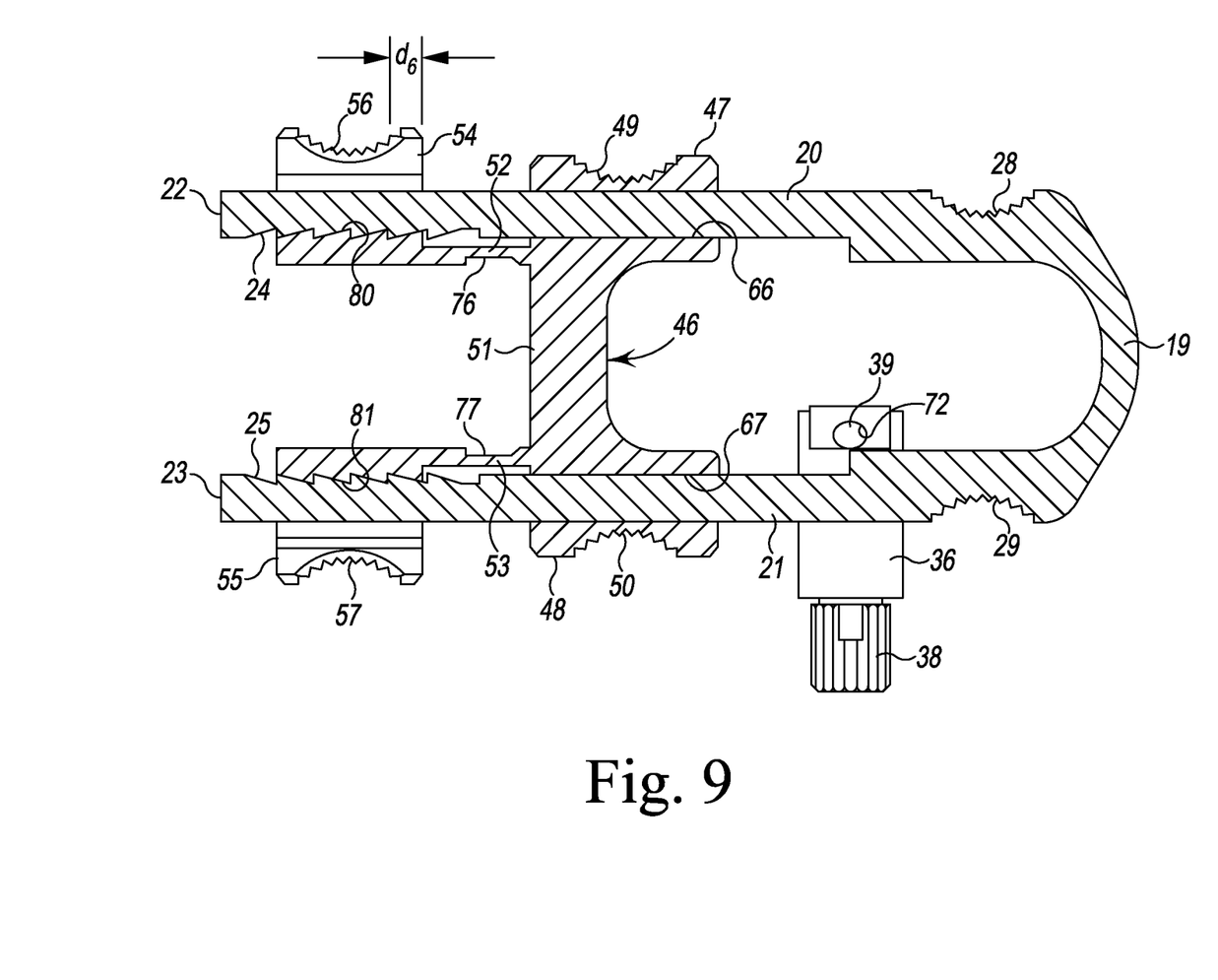
FIG. 9 is a sectional view of the surgical retractor of FIG. 8 taken along line 9-9 thereof.

As best seen in FIG. 9, an end 22 of the first tine 20 includes teeth, serrations or the like 24 on a lower surface thereof, while an end 23 of the second tine 21 includes teeth, serrations or the like 25 on an upper surface thereof, each forming a part of a ratchet or ratcheting mechanism that provides controlled movement and positional holding of the second retraction arm 14 relative to the first retraction arm 12. The interaction of the second retraction arm 14 relative to the first retraction arm 12 is discussed below.

The second retraction arm 14 is characterized by a carriage 46 defined by a generally U-shaped body 51 having an upper limb 47 and a lower limb 48. A depression or notch 49 is provided in the upper surface of the upper limb 47, the depression 49 preferably, but not necessarily, including serrations or the like to provide a gripping area. Likewise, a depression or notch 50 is provided in the lower surface of the lower limb 48, the depression 50 preferably, but not necessarily, including serrations or the like to provide a gripping area. The serrated depressions 49 and 50 allow a user to easily grasp or hold the carriage 46 during use.

The carriage 46 is movably supported on and by the first and second tines 20, 21 of the first retraction arm 12. Particularly, the upper limb 47 of the carriage body 51 has a bore 66 (see, e.g., FIGS. 7 and 9) that is shaped complementary to the shape of the first tine 20 such that the first tine 20 extends through the bore 66. The lower limb 48 of the carriage body 51 has a bore 67 (see, e.g., FIGS. 7 and 9) that is shaped complementary to the shape of the second tine 21 such that the second tine 21 extends through the bore 67. The carriage 46 thus slides or moves along the first and second tines 20, 21. Such movement is controlled by upper and lower ratchet/ratcheting mechanisms between the first retraction arm 12 and the second retraction arm 14. As indicated above, the first tine 20 has a first ratchet portion 24 of the upper ratchet/ratcheting mechanism that include serrations along the lower surface of the end 22 of the first tine 20, while the second tine 21 has a first ratchet portion 25 of the lower ratchet/ratcheting mechanism that include serrations along the upper surface of the end 23 of the second tine 21.

A second ratchet portion of the upper ratchet/ratcheting mechanism includes an upper, resilient finger 52 that extends from the end of the body 51 of the carriage 46 with an actuator 54 situated on the end of the resilient finger 52, the actuator 54 at least partially surrounding the end 22 of the first tine 20. The actuator 54 has a serrated notch 56 that provides an area to be grasped by a user's finger. As best seen in FIG. 9, the finger 52 is resilient through a reduced thickness portion 76 of the finger 52 allowing for flexibility and spring action of the finger 52 and thus the actuator 54 relative to the first tine 20. The actuator 54 has serrations 80 that face and mesh with the serrations 24 of the first tine 20. The finger 52 and the actuator 54 are normally biased in a latched position as shown in FIG. 9. Depressing the actuator 54 disengages the actuator serrations 80 from the serrations 24 of the first tine 20 to allow movement of the actuator 54 and thus the upper limb 47 of the carriage body 51.

A second ratchet portion of the lower ratchet/ratcheting mechanism includes a lower, resilient finger 53 that extends from the end of the body 51 of the carriage 46 with an actuator 55 situated on the end of the resilient finger 53, the actuator 55 at least partially surrounding the end 23 of the second tine 21. The actuator 55 has a serrated notch 57 that provides an area to be grasped by a user's finger. As best seen in FIG. 9, the finger 53 is resilient through a reduced thickness portion 77 of the finger 53 allowing for flexibility and spring action of the finger 53 and thus the actuator 55 relative to the second tine 21. The actuator 55 has serrations 81 that face and mesh with the serrations 25 of the second tine 21. The finger 53 and the actuator 55 are normally biased in a latched position as shown in FIG. 9. Depressing the actuator 55 disengages the actuator serrations 81 from the serrations 25 of the second tine 21 to allow movement of the actuator 55 and thus the lower limb 48 of the carriage body 51.

Figure 3:
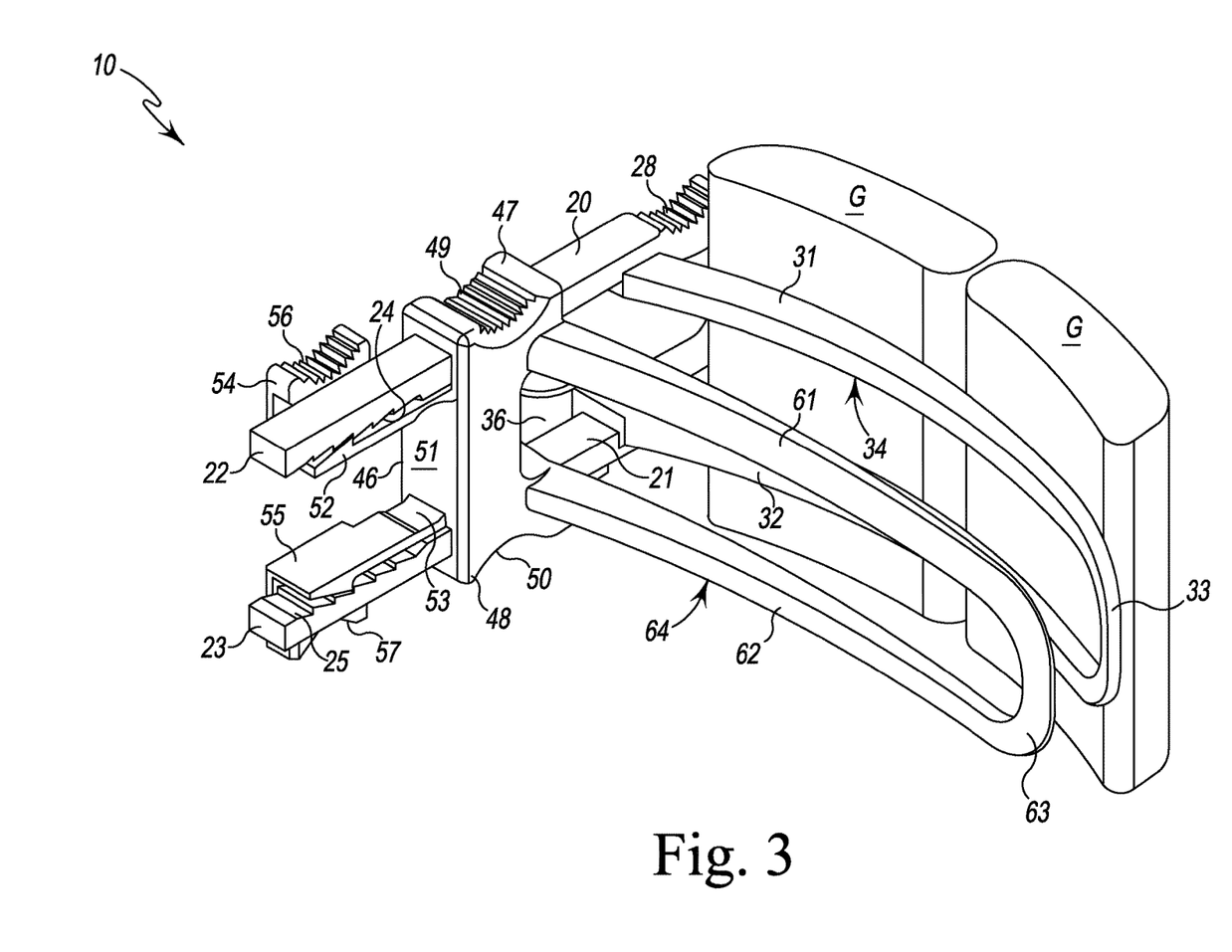
FIG. 3 is another isometric view of the surgical retractor of FIG. 1 shown in conjunction with a gastrocnemius muscle.

As best seen in FIG. 3, the second retraction arm 14 has a second blade 60 that extends outwardly from a side of the carriage 46. The second blade 60 is defined by a body 64 that generally forms a loop that extends from a side of the upper limb 47 of the carriage body 51 to a same side of the lower limb 48 of the carriage body 51, and defining an elongated "U" shape with an open interior. Particularly, the body 64 has an upper leg 61 that extends from the side of the upper limb 47 of the carriage body 51 to an arched end 63, and a lower leg 62 that extends from the side of the lower limb 48 of the carriage body 51 to the arched end 63. The body 64 defines a blade that is generally transverse to the carriage body 51 and the first and second tines 20, 21 but which preferably, but not necessarily, includes a curvature or bow (see additionally FIGS. 10-11) in order to be anatomically correct with respect to the muscle (tissue) that the blade 60 will contact. As such, and in keeping with the present surgical retractor 10 embodied as a gastrocnemius muscle G/soleus muscle S retractor, the blade 60 is curved in like manner as the soleus muscle S. The blade 60 is made with other curvature(s) or no curvature depending on the muscle (s) or muscle group(s) being retracted. In this manner, the present surgical retractor 10 may be anatomically designed such that the surgical retractor 10 is fit for a particular purpose and/or surgical procedure.

Figure 1:
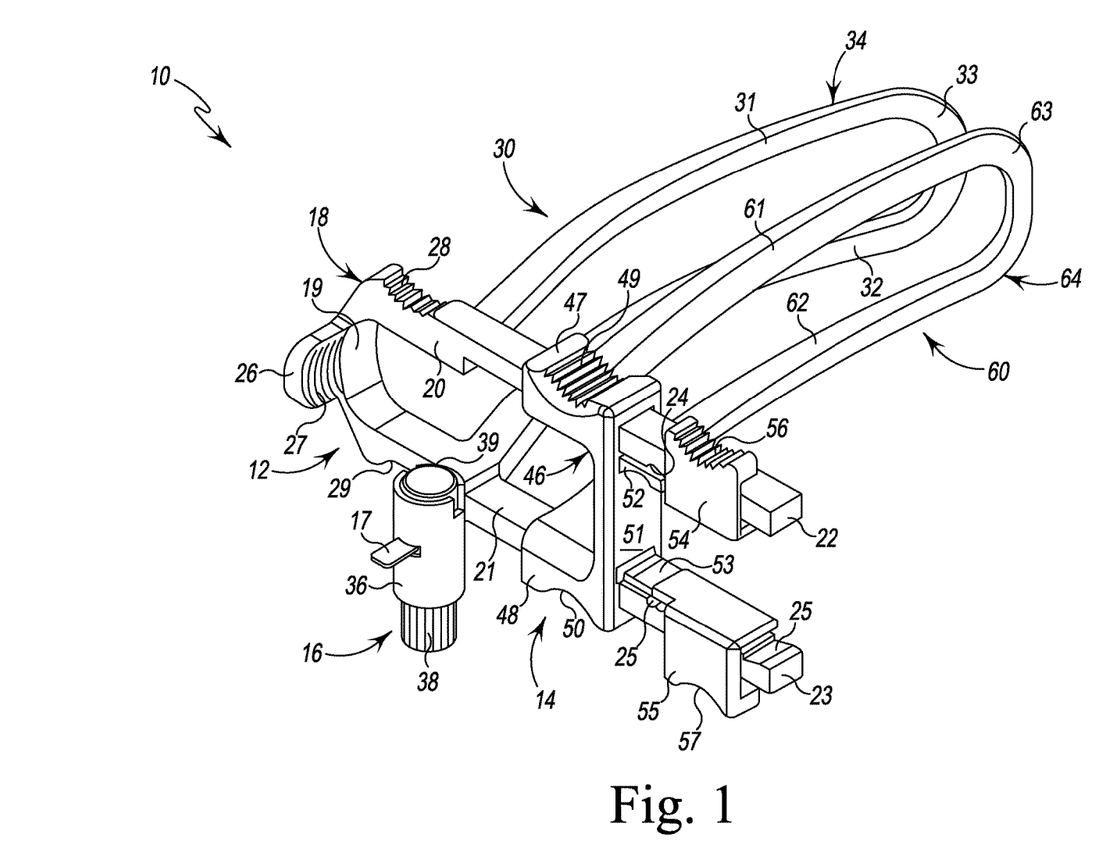
FIG. 1 is an isometric view of a surgical retractor fashioned in accordance with the present principles.
Figure 2:
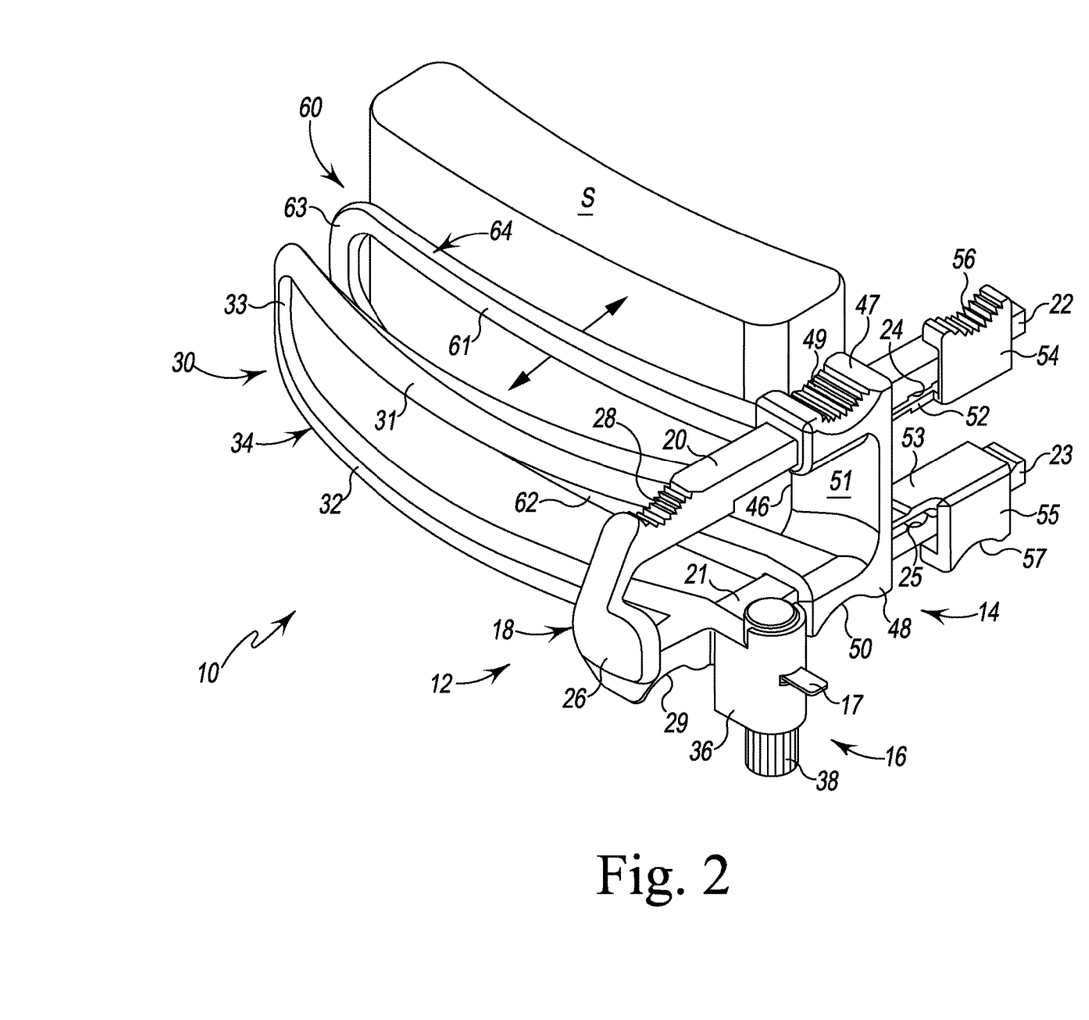
FIG. 2 is another isometric view of the surgical retractor of FIG. 1 shown in conjunction with a soleus muscle.

The carriage 46 and thus the blade 60 (the second retraction arm 14) is movable (adjustable) along the first and second tines 20, 21 of the first retraction arm 12. The carriage 46 moves freely in the retracting/opening direction (i.e. away from the second blade 30) by free ratcheting of the upper and lower ratchet mechanisms through spring action of actuators 54, 55. Movement in the un-retracting/closing direction (i.e. towards the second blade 30) however, requires manual actuation by depressing both actuators 54 and 55 to overcome the spring bias of the upper and lower ratchet mechanisms thereby releasing the ratchets and allow sliding movement of the carriage 46. Such movement is indicated by the two oppositely pointing arrows in FIGS. 2 and 5.

Figure 10:
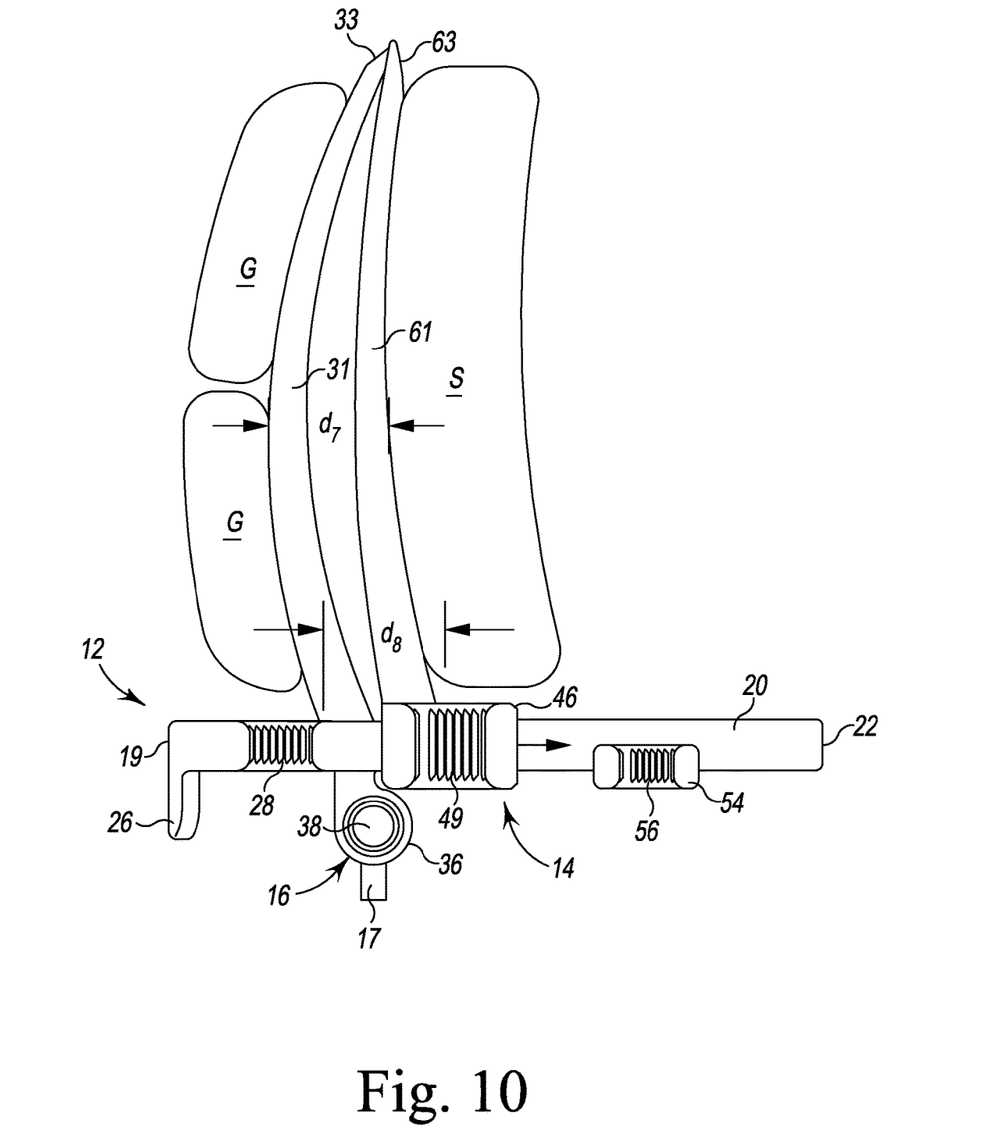
FIG. 10 is a top view of the surgical retractor of FIG. 1 relative to a soleus muscle and a gastrocnemius muscle, the surgical retractor in an un-retracted position.
Figure 11:
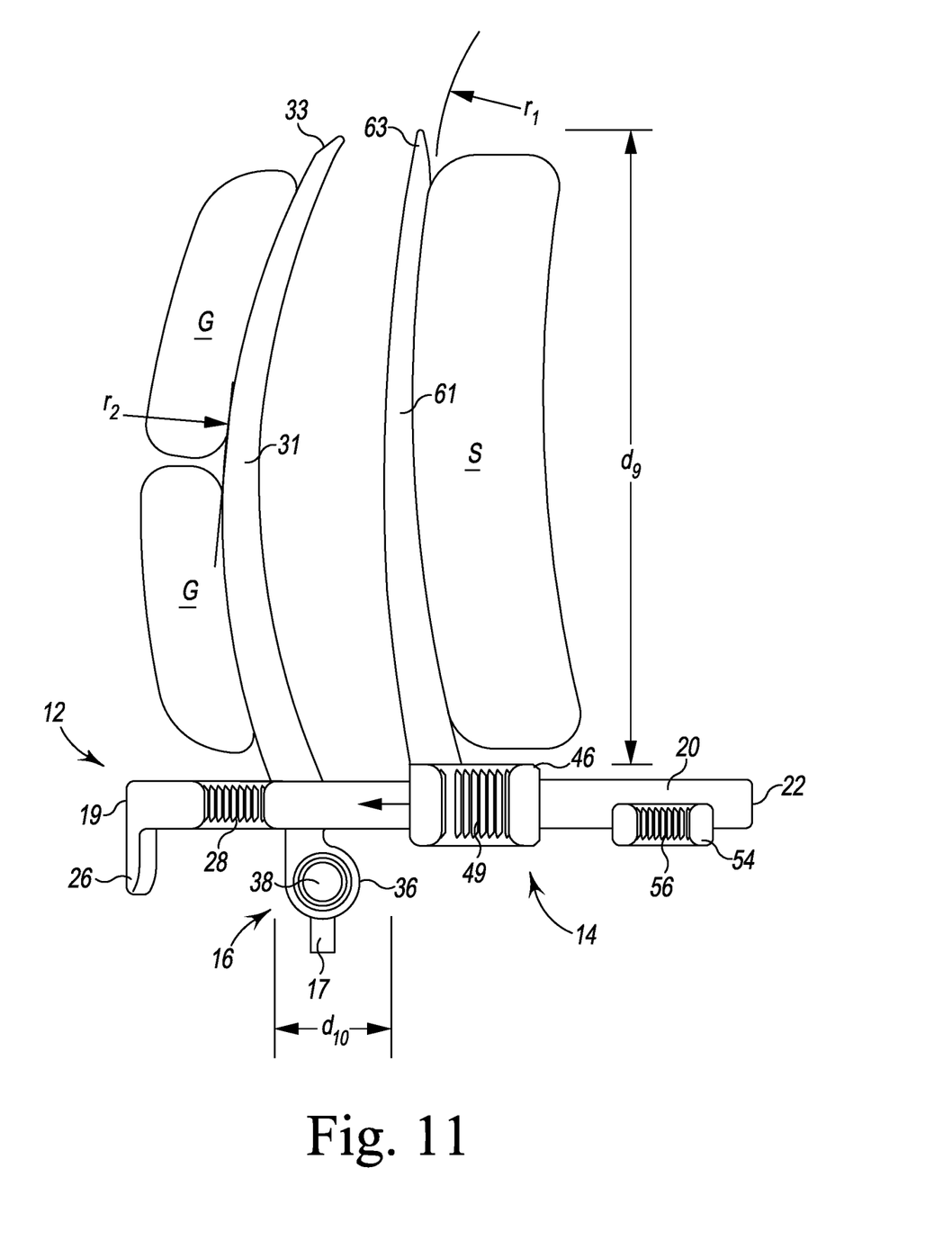
FIG. 11 is a top view of the surgical retractor as shown in FIG. 10 with the surgical retractor in a retracted position.

In FIG. 10, the surgical retractor 10 is in a fully un-retracted position as represented by the arrow extending from the left side of the carriage 46 towards the end 22 of the first tine 20 indicating that the carriage 46 and thus the blade 60 is movable away from the blade 30 to provide tissue retraction. In this position, the blade 60 is closest to the blade 30 and, in particular, the arched end 63 of the blade body 64 of the blade 60 abuts the arched end 33 of the blade body 34 of the blade 30. In FIG. 11, the surgical retractor 10 is in a retracted position as represented by the arrow extending from the right side of the carriage 46 towards the arced end segment 19 of the body 18 of the first retraction arm 12 indicating that the carriage 46 and thus the blade 60 is movable towards the blade 30 for un-retraction. In this position, the blade 60 is a distance from the blade 30.

Figure 5:
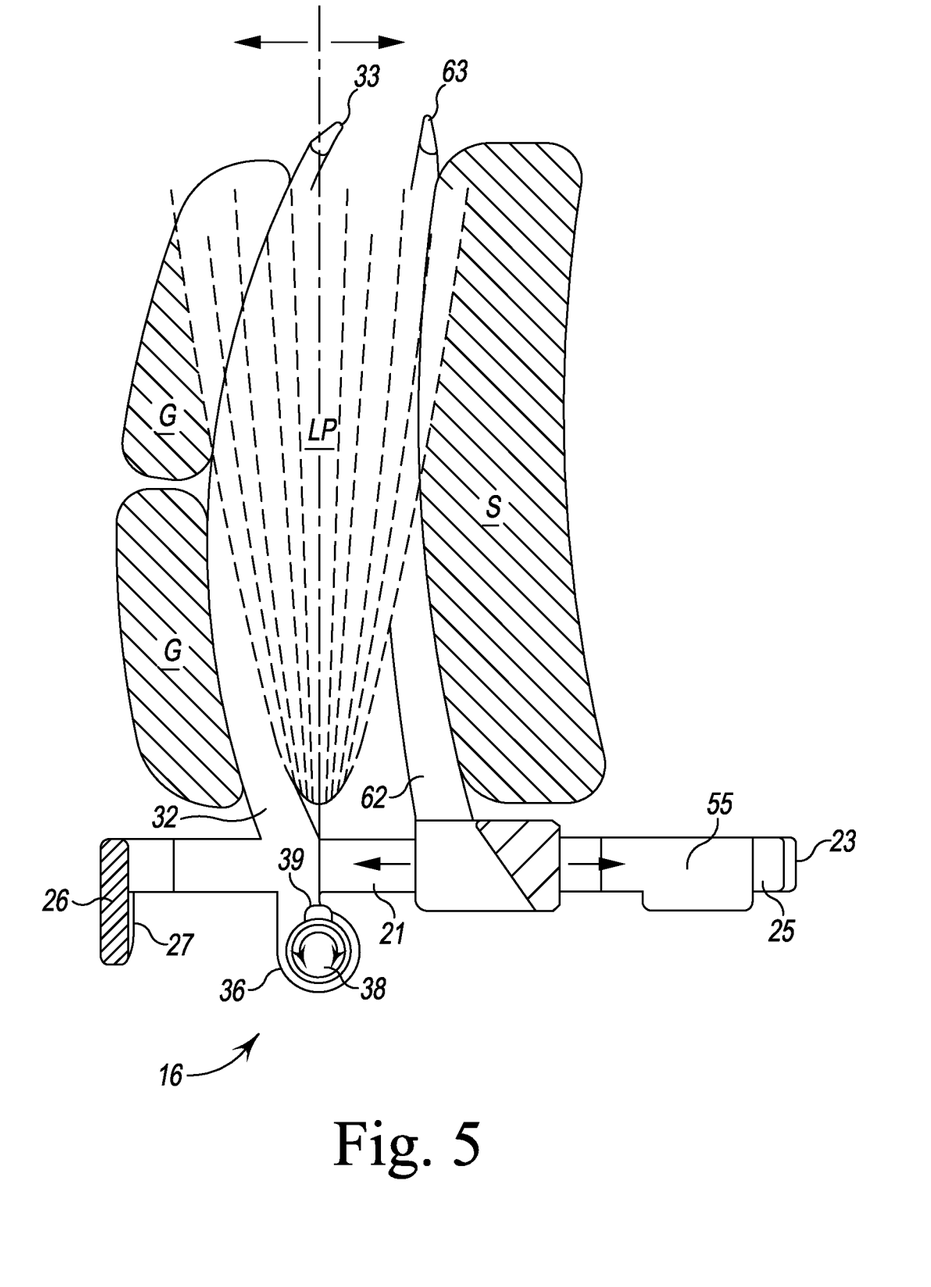
FIG. 5 is a view of the surgical retractor of FIG. 4 taken along line 5-5 thereof showing a light beam pattern from the light of the surgical retractor relative to retraction arms of the surgical retractor and to exemplary muscles being held by the retraction arms.
Figure 6:
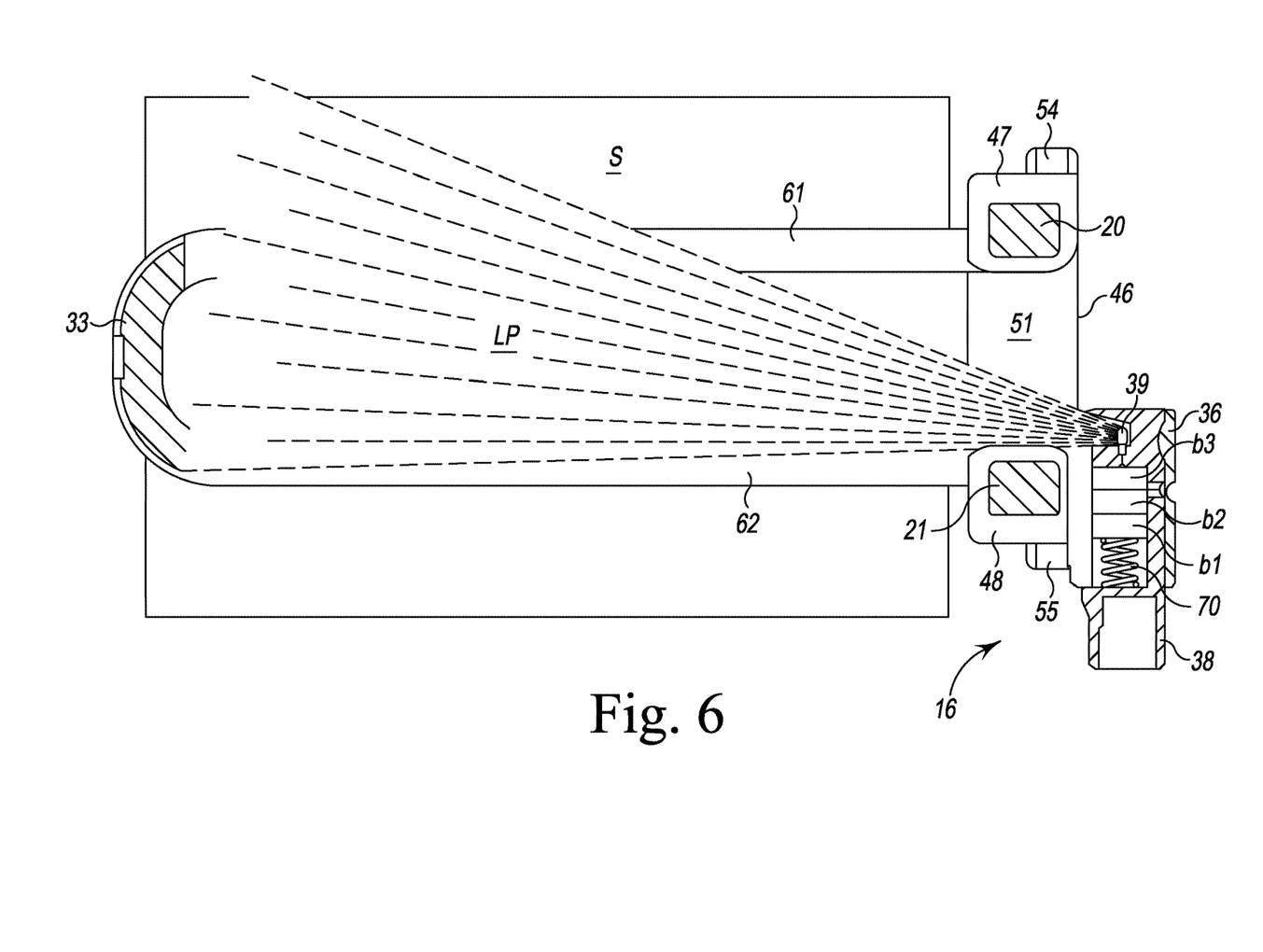
FIG. 6 is a sectional view of the surgical retractor of FIG. 4 taken along line 6-6 thereof showing the light beam pattern from the surgical retractor light and the light portion of the surgical retractor in sectional.

The light assembly 16 is carried on the first retraction arm 12. With reference to FIG. 6 the light assembly 16 is shown as having a generally cylindrical housing 36 that is situated on a side of the second tine 21 generally opposite the first blade 30. The housing 36 may take forms other than cylindrical as well as be positioned at different locations on and along the surgical retractor 10. In this form, and as best seen in FIG. 5, the housing 36 is situated opposite to where the lower leg 32 of the blade 30 joins the second tine 21. A light module or assembly 38 is releasably retained in the housing 36. A retention flange 41 helps retain the light module 38 in the housing 36. Particularly, the retention flange 41 is a small finger that protrudes out of the side of the light module 38 that will depress inwardly as it is pushed through the housing 36. Once completely through the housing 36, the flange 41 springs outwardly to lock the light module 38 in the housing 36. The light module 38 includes a light source 39 that is preferably, but not necessarily, a light emitting diode (LED). Other types of light sources may be used and are contemplated. However, an LED generates little heat that could interfere with the surgery and is thus preferred, but other low heat or no heat generating light sources may be used. The LED 39 is electrically connected to an electrical power source, embodied as three (3) disk style batteries b1, b2, b3 stacked upon one another to provide electrical contact between adjacent batteries. Other manners of providing electrical power may be used as well as other styles and/or number of batteries used. The batteries b1, b2, b3 are biased against one another for electrical contact via an electrically conducting spring 70 or the like that is, in turn, electrically connected to the LED 39 in order to complete an electrical circuit for turning on the light. An insulator 17 (not shown in FIGS. 5 and 6, as the light module 38 is depicted in FIGS. 5 and 6 in the on mode and therefore shining or projecting a beam of light LP), is provided that extends from the outside to the inside of the housing 36 and between the two batteries b2 and b3. The insulator 17 creates an open circuit to the light electrical circuit so that the light is normally off. Removal of the insulator 17 by pulling it out of the housing completes the light electrical circuit to turn the light on. This is accomplished during use of the surgical retractor 10. Other manners of interrupting and/or making contact between the batteries and the light source may be employed and are contemplated.

The light module 38 is able to be positioned so as to shine the light beam emanating from the light source of the light module 38 on or at a particular area of the surgical retractor 10 and/or on or at a particular tissue or tissue area. While this may be achieved in various manners, the light module 38 of the surgical retractor 10 is able to rotate relative to the housing 36, as indicated by the two-headed arrow on the top of the light module 38 of FIG. 5, such that the light beam or pattern LP (see FIGS. 5 and 6) can shine upon a particular area of the surgical retractor 10 and thus a particular area of a muscle G, S, blade 30, 60 or incision (as indicated by the two, oppositely pointing arrows at the top of the light beam LP of FIG. 5). Rotation of the light module 38 is accomplished by grasping the lower portion (essentially forming a knob) of the light module 38 that extends from the housing 36 and turning as desired.

Another or additional manner of achieving light beam positioning is to allow the light module 38, an equivalent thereof that holds the light source, or the light source itself, to move, slide or otherwise shift position along the surgical retractor 10 or a portion thereof. The light source may also move up or down, or angularly to likewise position the light beam. Still further manners are contemplated.

Various Figures include lines and arrows delineating dimensions, component or part tolerances, or other features and/or aspects regarding one form of the surgical retractor 10. It should be appreciated that these dimensions, component or part tolerances, or other features (e.g. specification of the surgical retractor) are exemplary and can change as necessary. For example, forms of the present surgical retractor 10 for muscles or tissues other than the gastrocnemius and soleus would necessitate a change in specification.

Figure 4:
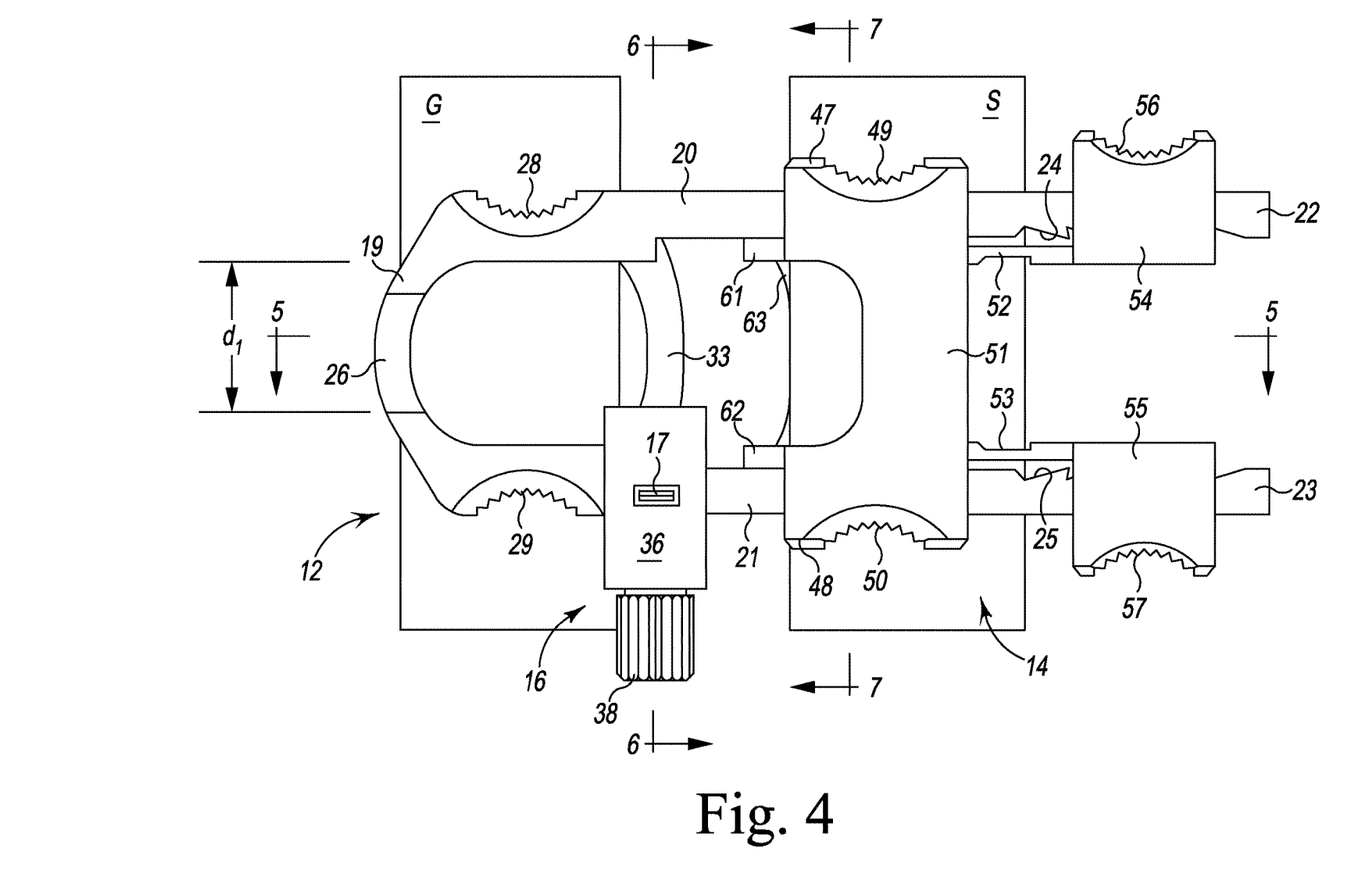
FIG. 4 is a side view of the surgical retractor of FIG. 1 shown in conjunction with both a soleus muscle and a gastrocnemius muscle.
Figure 7:
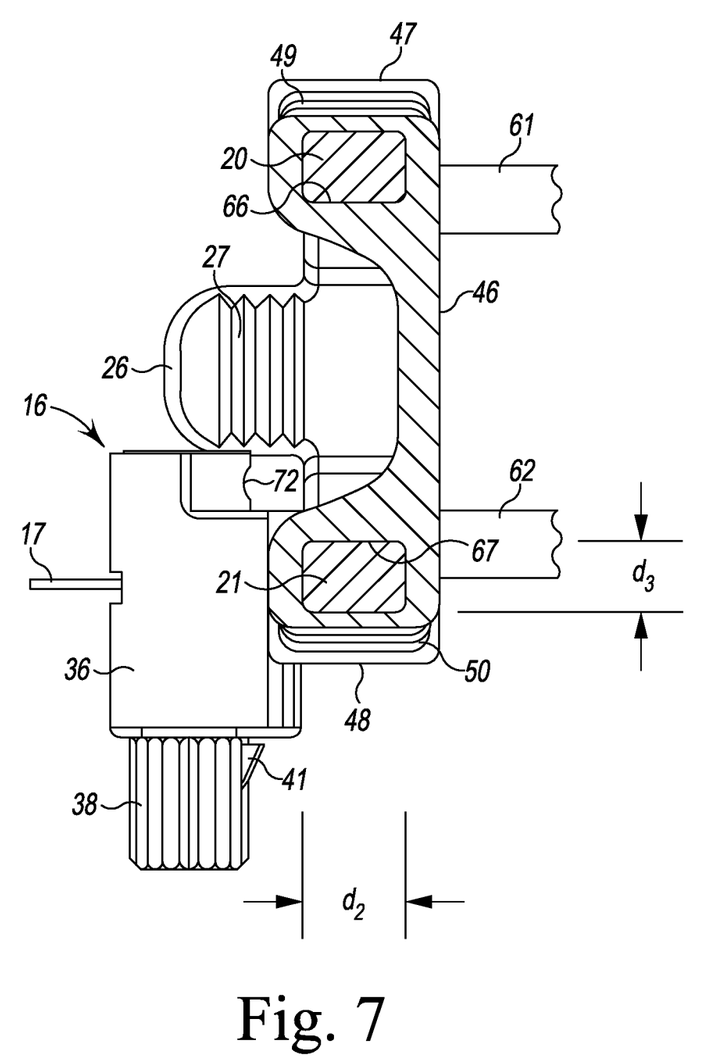
FIG. 7 is a sectional view of the surgical retractor of FIG. 4 taken along line 7-7 thereof.
Figure 8:
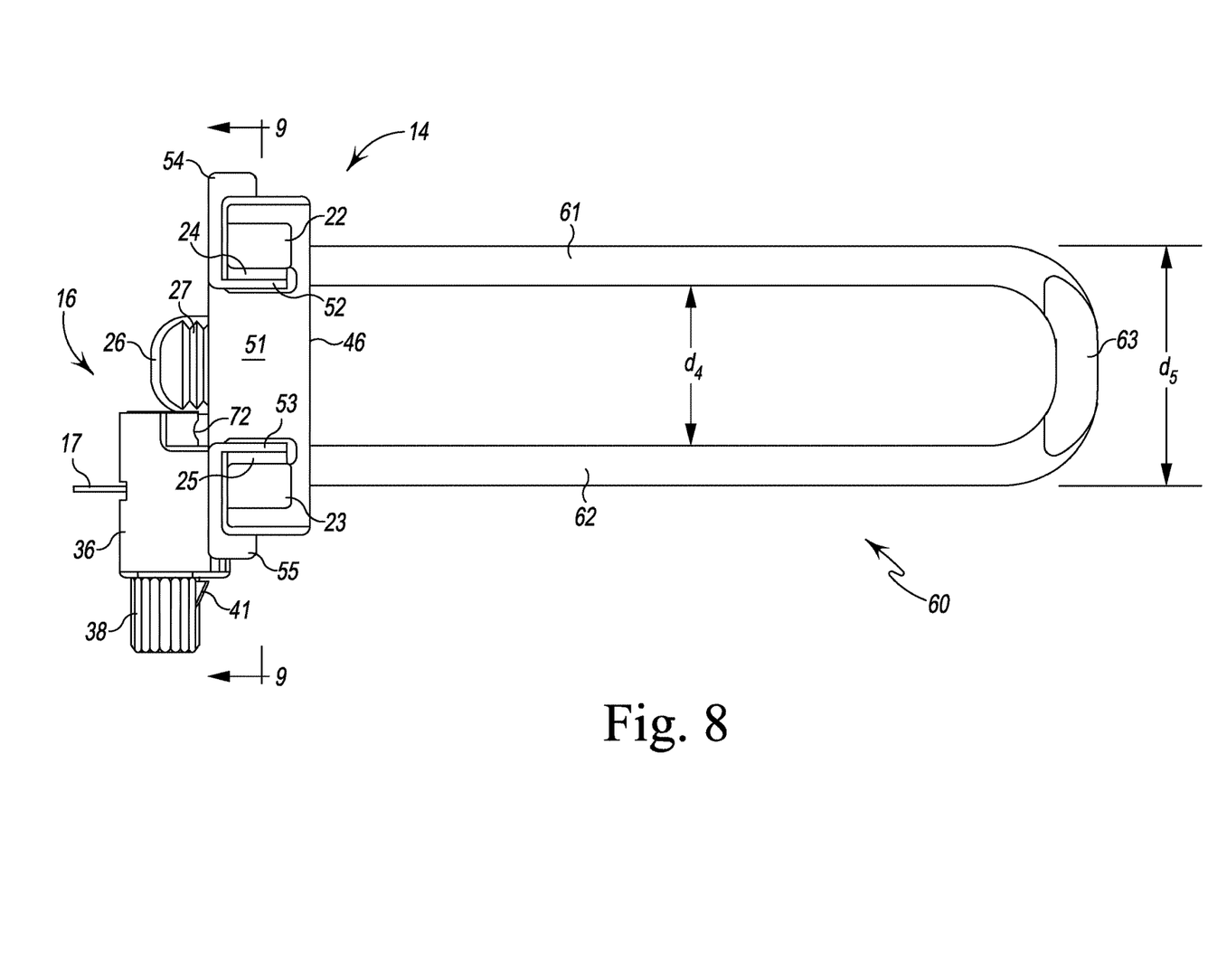
FIG. 8 is a side view of the surgical retractor of FIG. 1.

In FIG. 4, dimension $d_1$ corresponding to 0.784 inches (19.91 millimeters) is given for the distance between the top of the light housing 38 and the bottom of the first tine 20. In FIG. 7, dimension $d_2$ corresponding to 0.375 inches (9.53 millimeters) is given for the width of the second tine 21 (and of the first tine 20), while dimension $d_3$ corresponding to 0.250 (6.35 millimeters) is given for the height of the second tine 21 (and of the first tine 20). In FIG. 8, dimension of $d_4$ corresponding to 1.0 inches (25.4 millimeters) is given for the distance between the bottom of the upper leg 61 and the top of the lower leg 62 of the blade 60, while dimension of $d_5$ corresponding to 1.50 inches (38.1 millimeters) is given for the distance between the top of the upper leg 61 and the bottom of the lower leg 62 of the blade 60. In FIG. 9, dimension of $d_6$ corresponding to 0.200 inches (5.08 millimeters) is given for ratchet pitch for the serrations 24 of the first tine 20 and the serrations 80 of the finger 52 forming an upper ratchet mechanism, and for the serrations 25 of the second tine 21 and the serrations 81 of the finger 53 forming a lower ratchet mechanism.

In FIG. 10, dimension $d_7$ corresponding to 0.911 inches (23.13 millimeters) is given for the width of the blades 30 and 60 at a line between the two arrows illustrating incision insertion width when the surgical retractor 10 is in the closed position, while dimension $d_8$ corresponding to 0.931 inches (23.64 millimeters) of width of the blades 30 and 60 at a line between the two arrows illustrating maximum retraction width when the surgical retractor 10 is in the closed position. In FIG. 11, dimension $d_9$ corresponding to 4.906 inches (124.62 millimeters) is given for the length of the blade 60, and a radius $r_1$ corresponding to 11.394 inches (289.42 millimeters) is given for the radius of curvature of the blade 60, dimension $d_{10}$ corresponding to 1.50 inches (38 millimeters) is given for the distance or length of retraction of the blade 60 relative to the blade 30 (tissue), and a radius $r_2$ corresponding to 5.89 inches (149.6 millimeters) is given for the radius of curvature of the blade 30.

The surgical retractor 10 is preferably, but not necessarily, ergonomically designed so that it can be inserted into a patient's incision by utilizing one's left or right hand. Particularly, when the surgical retractor 10 is in the closed or un-retracted position, the blades 30 and 60 are inserted into the incision. After insertion of the blades 30, 60, the grooved tab 26 of the first retractor portion 12 is manipulated by the thumb while the second retractor portion 14 is grasped by the other hand. The surgical retractor 10 is manually retracted by the user to move the blade 60 away from the blade 30 to create a gap between the blades 30 and 60 for scalpel clearance. The upper and lower ratchet mechanisms incrementally ratchet along the first and second tines, preventing back movement of the carriage, and temporarily fixing position of the carriage and thus the second blade relative to the first blade. When the actuators 54, 55 are released, the upper and lower ratchet mechanisms will automatically hold the carriage 46 of the second retraction portion 14 and thus the blade 60 of the second retraction portion 14 relative to the first and second tines 20, 21 of the first retraction portion 14 and thus the blade 30 during surgery. The LED is actuated by removing the plastic insulator 17 that protrudes form the side of the housing 36. This may be done before the blades 30, 60 are inserted into the incision. The LED is manipulated as appropriate to shine the light beam onto the desired incision area, muscle (tissue) and/or blade. Manipulation of the LED may be done as much as needed. Manipulation of the actuator 54, 55 releases the associated ratchets to allow the carriage 46 of the second retractor portion 14 and thus the blade 60 to be returned manually to a closed position. Other manners of utilizing the present surgical retractor 10 are contemplated and consistent with the present teachings.

While the invention has been illustrated and described in detail in the foregoing drawings and description, the same is to be considered as illustrative and not restrictive in character, it being understood that only an illustrative form thereof has been show and described and that all changes and modifications that are within the scope of the following claims are desired to be protected.

What is claimed is:

1. A surgical retractor comprising:
a body having a first end, a first tine extending from one side of the first end, the first tine having a first ratchet portion, a second tine extending from a second side of the first end, the second tine having a second ratchet portion, and a first blade extending from the first and second tines, the first blade fashioned as a loop defining a first open interior;
a carriage carried for movement on and along the first and second tines, the carriage having a second blade extending from a side of the carriage, a first resilient finger extending from a first end of the carriage along the first tine and having a first catch that is normally biased by the resiliency of the first resilient finger to cooperate with the first ratchet portion of the first tine to allow free movement of the carriage in a first direction along the first tine but prevent movement of the carriage in a second direction along the first tine, but which may be manually actuated to overcome the resiliency of the first resilient finger to allow free movement of the carriage in the second direction with respect to the first tine, a second resilient finger extending from a second end of the carriage along the second tine and having a second catch that is normally biased by the resiliency of the second resilient finger to cooperate with the second ratchet portion of the second tine to allow free movement of the carriage in the first direction along the second tine but prevent movement of the carriage in the second direction along the first tine, but which may be manually actuated to overcome the resiliency of the second resilient finger to allow free movement of the carriage in the second direction with respect to the second tine; and
a light source and battery mounted on the body, the light source emitting a light beam when actuated by the battery, the light beam of which may be positioned to direct the light beam towards a desired area.

2. The surgical retractor of claim 1, wherein light source is positioned to direct light from the light source through rotation.

3. The surgical retractor of claim 2, wherein the light source comprises an LED.

4. The surgical retractor of claim 1, wherein:
the first blade comprises a first, elongated U-shaped rail extending from the first tine to the second tine; and
the second blade comprises a second, elongated U-shaped rail extending from a top side of the side of the carriage to a bottom of the side of the carriage.

5. The surgical retractor of claim 4, wherein:
the first, elongated U-shaped rail has an anatomically correct curvature for a first particular muscle of the body; and
the second, elongated U-shaped rail has an anatomically correct curvature for a second particular muscle of the body.

6. A surgical retractor comprising:
a first retraction portion;
a first blade extending from the first retraction portion to a first tip of the first blade;
a second retraction portion movably carried on the first retraction portion;
a second blade extending from the second retraction portion to a second tip of the second blade, wherein, the first blade and the second blade are shaped such that, in an un-retracted position, the first tip touches the second tip and a gap exists between the first blade and the second blade, between the first and second tips and the first retractor portion;
a first ratchet assembly formed on and between a first section of the first retraction portion and a first section of the second retraction portion, the first ratchet assembly spring biased to allow free travel of the first section in a first direction but limit movement of the first section in a second direction and fix position of the first section of the second retraction portion relative to the first section of the first retraction portion but, upon manual actuation of the second ratchet assembly, allows travel of the first section of the second retraction portion relative to the first section of the first retraction portion in the second direction;
a second ratchet assembly formed on and between a second section of the first retraction portion and a second section of the second retraction portion, the second ratchet assembly spring biased to allow free travel of the second section in the first direction but limit movement of the second section in the second direction and fix position of the second section of the second retraction portion relative to the second section of the second retraction portion but, upon manual actuation of the second ratchet assembly, allows travel of the second section of the second retraction portion relative to the second section of the first retraction portion in the second direction; and
a light assembly supported on the first retraction portion and having a rotatable light source and a battery operably connected to the light source, the light source manually movable to position a light beam from the light source as desired.

7. The surgical retractor of claim 6, wherein:
the first ratchet assembly includes a first resilient finger extending from the second retraction portion and having a first catch that is normally biased by the resiliency of the first resilient finger to cooperate with first teeth of the first section of the first retraction portion to fix position of the first section of the second retraction portion with respect to the first section of the first retraction portion but which allows travel of the first section of the second retraction portion with respect to the first section of the first retraction portion upon manual actuation of the first catch; and
the second ratchet assembly includes a second resilient finger extending from the second retraction portion and having a second catch that is normally biased by the resiliency of the second resilient finger to cooperate with second teeth of the second section of the first retraction portion to fix position of the second section of the second retraction portion with respect to the second section of the first retraction portion but which allows travel of the second section of the second retraction portion with respect to the second section of the first retraction portion upon manual actuation of the second catch.

8. The surgical retractor of claim 7, wherein the first retraction portion comprises:
a body with an arched end;
a first tine extending from one end of the arched end;
a second tine extending from anther end of the arched end;
first teeth on the first tine forming part of the first ratchet assembly; and
second teeth on the second tine forming part of the second ratchet assembly.

9. The surgical retractor of claim 8, wherein the first blade extends generally transverse from the first and second tines.

10. The surgical retractor of claim 8, further comprising:
third teeth on the first catch forming part of the first ratchet assembly; and
fourth teeth on the second catch forming part of the second ratchet assembly.

11. The surgical retractor of claim 8, wherein:
the first blade comprises a first, elongated U-shaped rail extending from the first tine to the second tine; and
the second blade comprises a second, elongated U-shaped rail extending from the first section of the second retraction portion to the second section of the second retraction portion.

12. The surgical retractor of claim 11, wherein:
the first, elongated U-shaped rail has an anatomically correct curvature for a first particular muscle of the body; and
the second, elongated U-shaped rail has an anatomically correct curvature for a second particular muscle of the body.

13. The surgical retractor of claim 12, wherein the body, the first and second tines, the first, elongated U-shaped rail, the carriage, the second, elongated U-shaped rail, the first resilient finger, and the second resilient finger are formed of plastic.

14. The surgical retractor of claim 7, wherein the light source comprises an LED.

15. A surgical retractor comprising:
a first retraction arm;
a second retraction arm slidably coupled to the first retraction arm;
a first blade extending generally transverse from a first side of the first retraction arm to define a first base adjacent to the first side of the first retraction arm and a first tip displaced from the first side of the first retraction arm; and
a second blade extending generally transverse from a first side of the second retraction arm generally alongside the first blade, to define a second base adjacent to the first side of the second retraction arm and a second tip displaced from the first side of the second retraction arm;
wherein:
sliding the second retraction arm along the first retraction arm in a first un-retracted direction causes the second blade to move toward the first blade,
sliding the second retraction arm along the first retraction arm in a second retracted direction causes the second blade to move away from the first blade,
the first blade curves toward the second blade such that the first tip is displaced along the second retracted direction, relative to the first base; and
the second blade curves away from the first blade such that the second tip is displaced along the second retracted direction, relative to the second base.

16. The surgical retractor of claim 15, wherein, in an un-retracted position, the first tip touches the second tip and a gap exists between the first blade and the second blade, proximal to the first tip and the second tip.

17. The surgical retractor of claim 15, wherein the first tip of the first blade curves toward the second tip of the second blade at a first radius of curvature and the second tip of the second blade curves away from the first tip of the first blade at a second radius of curvature.

18. A surgical retractor comprising:
a first retraction arm;
a second retraction arm slidably coupled to the first retraction arm;
a first blade extending generally transverse from a first side of the first retraction arm to a first tip of the first blade; and
a second blade extending generally transverse from a first side of the second retraction arm to a second tip of the second blade, the second blade extending generally alongside the first blade;
wherein:
sliding the second retraction arm along the first retraction arm in a first un-retracted direction causes the second blade to move toward the first blade;
sliding the second retraction arm along the first retraction arm in a second retracted direction causes the second blade to move away from the first blade,
the first blade curves to define a concave surface facing the second blade; and
the second blade curves to define a convex surface facing the first blade.

19. The surgical retractor of claim 18, wherein, in an un-retracted position, the first tip touches the second tip and a gap exists between the first blade and the second blade, proximal to the first tip and the second tip.

20. The surgical retractor of claim 18, wherein:
the first tip of the first blade curves toward the second tip of the second blade at a first radius of curvature and the second tip of the second blade curves away from the first tip of the first blade at a second radius of curvature; and
the first radius of curvature is less than the second radius of curvature.

* * * * *